United States Patent [19]

Levin

[11] Patent Number: 5,298,517
[45] Date of Patent: Mar. 29, 1994

[54] ANGIOTENSIN II RECEPTOR BLOCKING AGENTS

[75] Inventor: Jeremy I. Levin, Nanuet, N.Y.

[73] Assignee: American Cyanamid Company, Wayne, N.J.

[21] Appl. No.: 133,686

[22] Filed: Oct. 7, 1993

[51] Int. Cl.$^5$ .................... A61K 31/42; C07D 261/20
[52] U.S. Cl. .................... 514/379; 514/291; 514/338; 548/241; 546/89; 546/92; 546/270
[58] Field of Search ............. 548/241; 514/379, 338, 514/291; 546/270, 89, 92

[56] References Cited

U.S. PATENT DOCUMENTS 5,138,069  8/1992  Carini et al. .................... 548/253

FOREIGN PATENT DOCUMENTS

0253310A2  1/1988  European Pat. Off. ............ 548/241

OTHER PUBLICATIONS

CA117 (5): 48554v Preparation . . . antagonists. Narr et al., p. 936, 1992.

*Primary Examiner*—M. Lee
*Assistant Examiner*—Joseph K. McKane
*Attorney, Agent, or Firm*—T. S. Szatkowski

[57] ABSTRACT

This disclosure describes novel imidazole compounds having the formula:

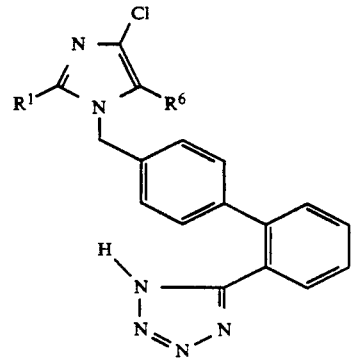

FORMULA I wherein $R^1$ and $R^6$ are described in the specification which have activity as angiotensin II (AII) antagonists.

9 Claims, No Drawings

ANGIOTENSIN II RECEPTOR BLOCKING AGENTS

BACKGROUND OF THE INVENTION

1. Field of the Invention

This invention relates to certain imidazole compounds which have demonstrated activity as angiotensin II (AII) antagonists and are therefore useful in alleviating angiotensin induced hypertension and for treating congestive heart failure.

SUMMARY OF THE INVENTION

According to the present invention, there are provided novel compounds of Formula I which have angiotensin II antagonizing properties and are useful as hypertensives:

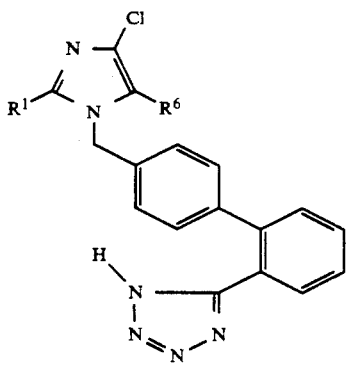

FORMULA I wherein:

$R^1$ is lower alkyl of 1 to 4 carbon atoms;

$R^6$ is

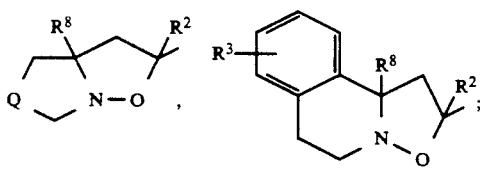

$R^2$ is hydrogen, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridinyl, thienyl, furanyl;

$R^8$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), $-CO_2R^7$;

$R^7$ is H, straight or branched chain lower alkyl of 1 to 4 carbon atoms;

Q is $-(CR^8R^8)_n-$;

n is 1 or 2;

$R^3$ is H, $-CH_3$, $-CF_3$, nitro, $-OCH_3$, F, Cl, Br;

or the pharmaceutically acceptable salts thereof.

The present invention also provides novel intermediate compounds, methods for making the novel imidazole angiotensin II antagonizing compounds and methods of using the novel quinazolinone angiotensin II antagonizing compounds to treat hypertension, congestive heart failure an to antagonize the effects of angiotensin II.

DETAILED DESCRIPTION OF THE INVENTION

The novel compounds of the present invention are prepared according to the following reaction schemes.

Referring to Scheme I, the 2-lower alkyl-4-chloro-1-[[2'-(1H-tetrazol-5-yl)[1,1'-biphenyl]-4-yl]methyl]-1H-imidazole-5-methanol 1 as the potassium salt, where $R^1$ is hereinbefore defined, is reacted with trityl chloride 2 in the presence of triethylamine in methylene chloride at reflux to provided protected intermediate 3. Intermediate 3 is oxidized with manganese dioxide in 1,2-dichloroethane to give aldehyde 4, where $R^1$ is hereinbefore defined, using the conditions of Ho-Shen Lin, Ashraff A. Rampersaud, Karen Zimmerman, Mitchell I. Steinberg, and Donald B. Boyd, J. Med. Chem. 35, 2658(1992). The aldehyde 4 is reacted with methylmagnesium bromide to give the desired secondary alcohol 6. Aldehyde 4 may also be reacted with the phosphorane to give olefin 5. Alcohol 6 is oxidized with manganese dioxide in 1,2-dichloroethane to give ketone 7. The ketone 7 is reacted with Grignard reagents $R^2MgBr$ where $R^2$ is hereinbefore defined, except hydrogen, to give the desired alcohol 8. The alcohol 8 is dehydrated with {bis[a,a-bis(trifluoromethyl)benzenemethanolato]-diphenylsulfur} or with sulfuric, hydrochloric, or p-toluenesulonic acid to give olefin 9. The olefin 9 where $R^1$ and $R^2$ are hereinbefore defined is reacted with nitrone 11 to give bicyclic derivative 14. Additionally, olefin 9 is reacted with nitrone 13 to give tricyclic derivative 15. Nitrones 11 and 13 are prepared from 10 and 12 respectively by using the hydrogen peroxide-selenium dioxide method of S-I. Murahaski and T. Shiota, Tet. Letters, 28(21) 2383 (1987). Deprotection of the trityl group is accomplished by refluxing an aqueous acetone solution of the bicyclic derivative 14 or tricyclic derivative 15 with a catalytic amount of hydrochloric acid or other suitable acid such as sulfuric, trifluoroacetic or hydrogen chloride for 2-24 hours. Alternatively, heating 14 or 15 in tetrahydrofuran-methanol removes the trityl protecting group and affords 16 or 17 respectively.

SCHEME I
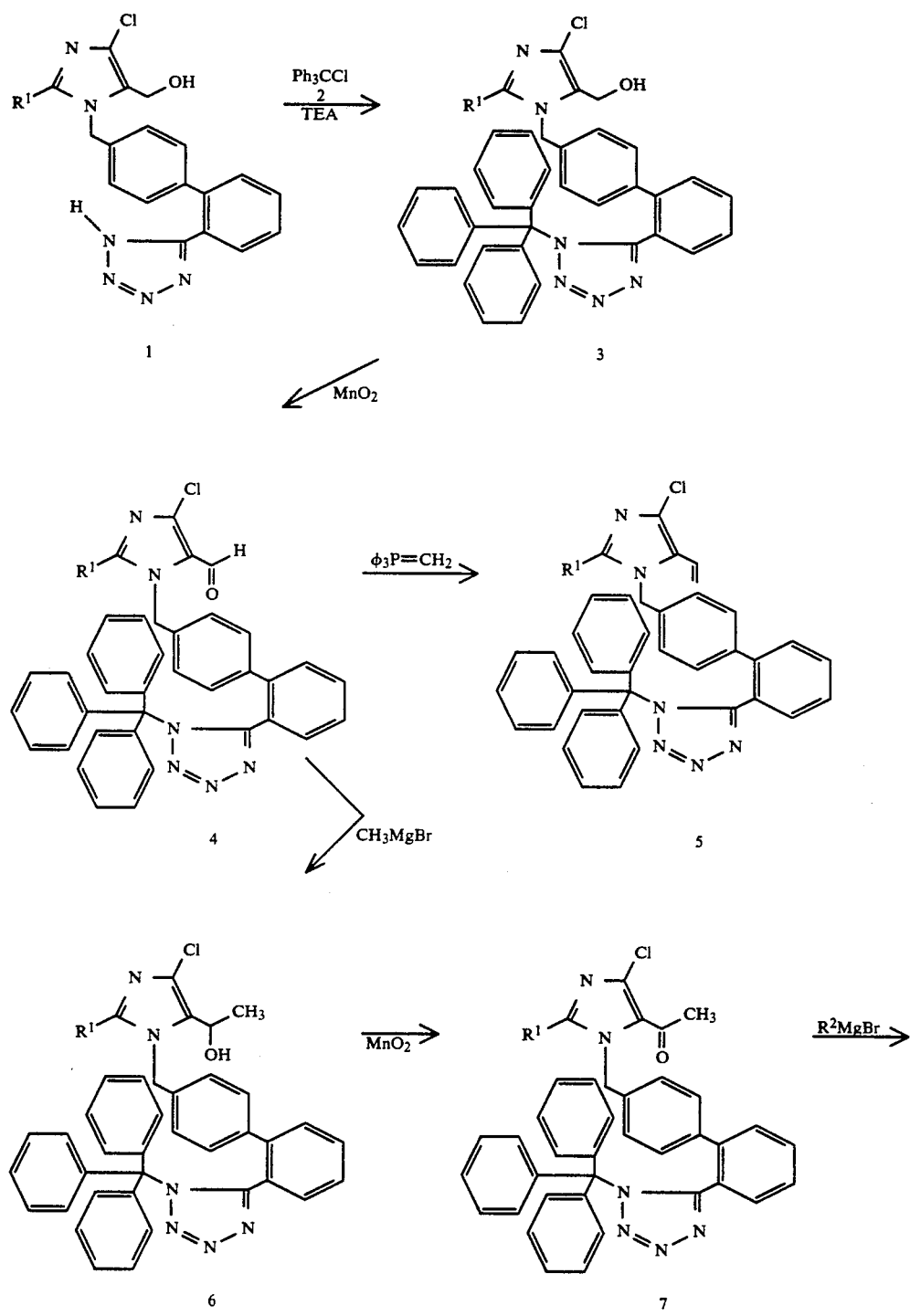

-continued
SCHEME I
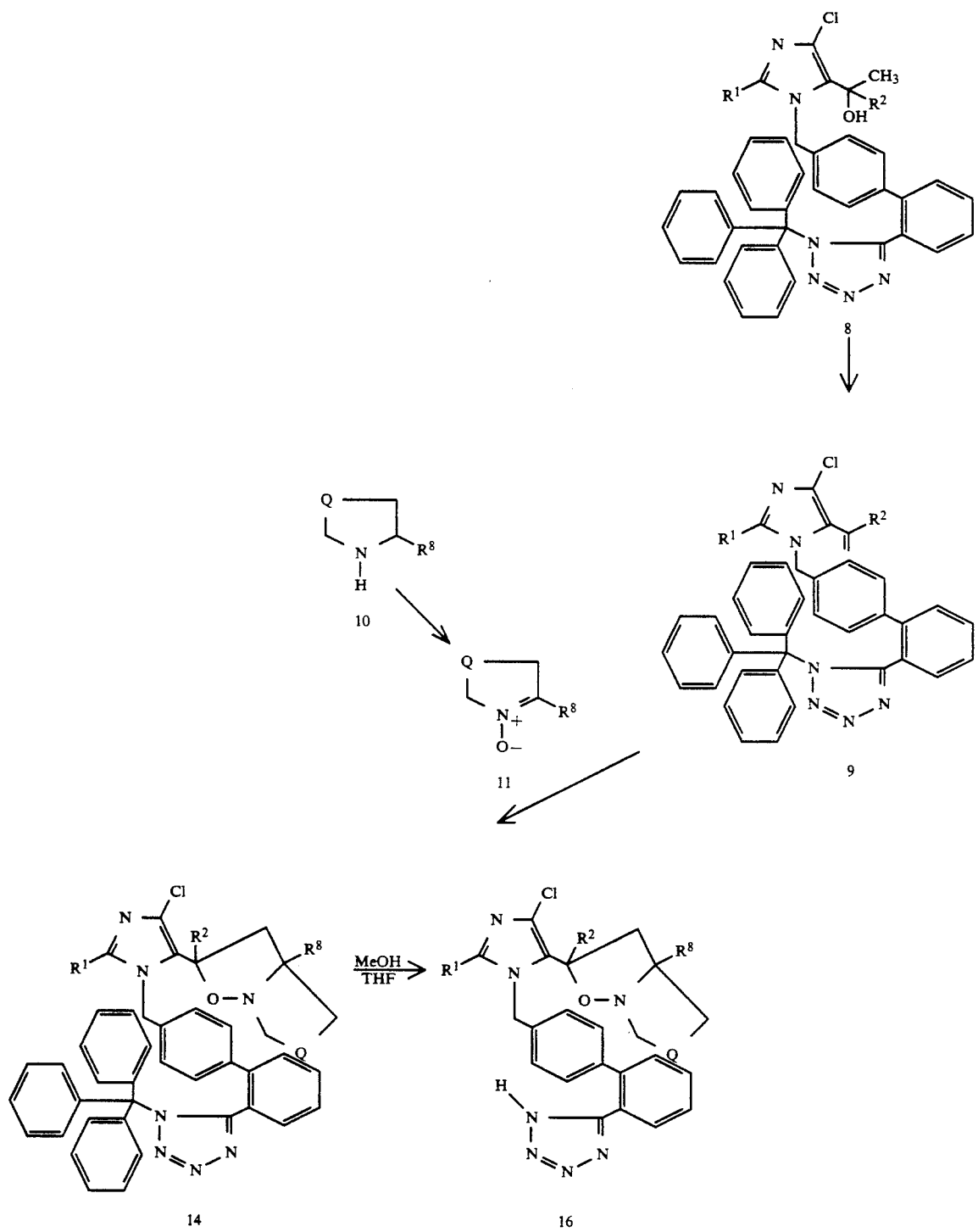

SCHEME 1 -continued

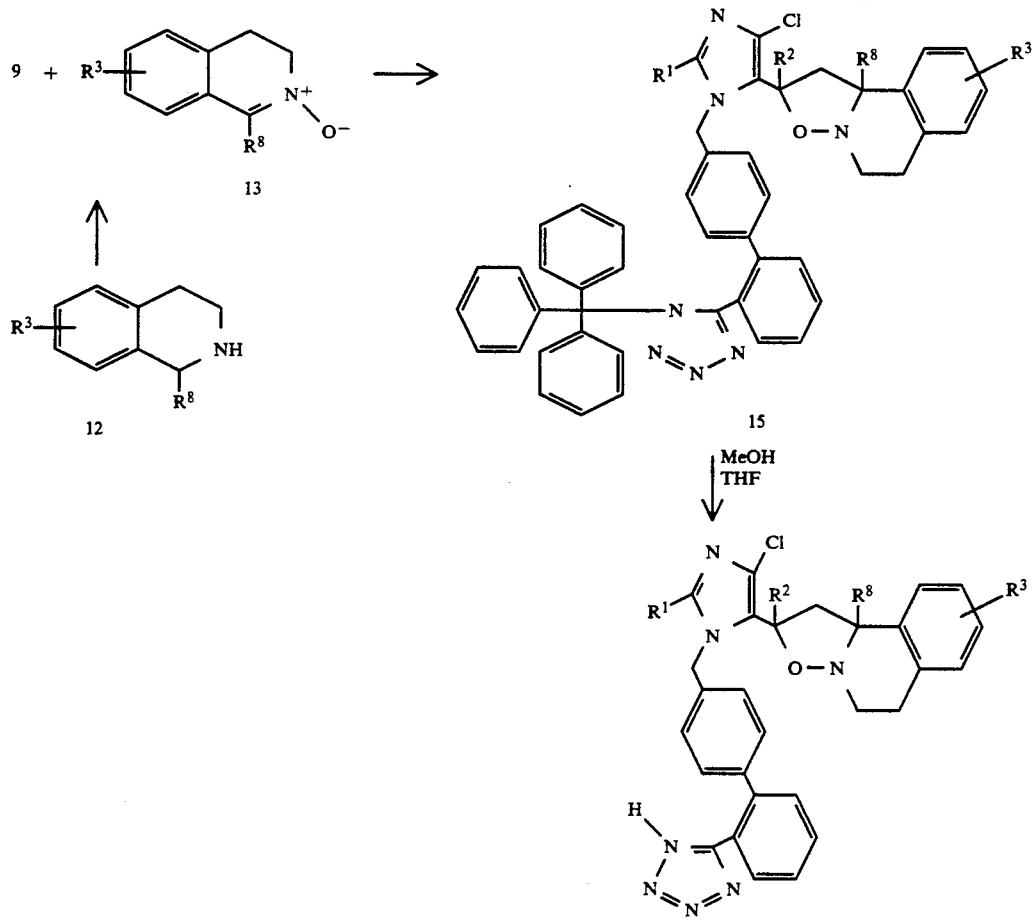

Reactions are performed in a solvent appropriate to the reagents and materials employed and suitable for the transformation being effected. It is understood by those skilled in the art of organic synthesis that the various functionalities present on suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Pharmaceutically suitable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability flowability, hydroscopicity and solubility. Preferred salts of this invention for the reasons cited above include potassium, sodium, calcium, magnesium and ammonium salts.

Some of the compounds of the hereinbefore described schemes have centers of symmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

While the invention has been illustrated using the trityl protecting group on the tetrazole, it will be apparent to those skilled in the art that other nitrogen protecting groups may be utilized. Contemplated equivalent protecting groups include, benzyl, p-nitrobenzyl, propionitrile or any other protecting group suitable for protecting the tetrazole nitrogen. Additionally, it will be apparent to those skilled in the art that removal of the various nitrogen protecting groups, other than trityl, may require methods other than dilute acid.

The compound of this invention and their preparation are illustrated in the following nonlimiting examples.

EXAMPLE 1

2-Butyl-4-chloro-1-[[2'-[1-(triphenylmethyl)-1H-tetrazol-5-yl][1,1'-biphenyl]-4-yl]methyl]-1H-imidazole-5-methanol To a solution of 0.600 g of 2-butyl-4-chloro-1-[[2'-(1H-tetrazol-5-yl)[1,1'-biphenyl]-4-yl]methyl]-1H- imidazole-5-methanol mono potassium salt in 40 ml of methylene chloride is added 0.218 ml of triethylamine and 0.381 g of trityl chloride. The solution is heated at reflux for 8 hours, cooled and diluted with 30 ml of water. The organic layer is separated and the aqueous layer extracted with methylene chloride. The combined extracts are washed with water, dried with potassium carbonate, filtered and concentrated in vacuo to give 0.785 g of the desired product as a solid. FAB MASS SPEC 665(M+H).

EXAMPLE 2

2-Butyl-4-chloro-1-[[2'-[1-(triphenylmethyl)-1H-tetrazol-5-yl][1,1'-biphenyl]-4-yl]methyl]-1H-imidazole-5-carboxaldehyde A suspension of 0.765 g of the product of Example 1 in 20 ml of 1,2-dichloroethane is sonicated under argon for 18 hours with 0.517 g of manganese dioxide. An additional 2 g of manganese dioxide is added and sonication continued for 2 hours. The reaction reaction mixture is filtered through diatomaceous earth which is washed with 500 ml of methylene chloride. The filtrate is concentrated in vacuo to give 0.696 g of the desired product as a solid. FAB MASS SPEC 685(M+Na).

EXAMPLE 3

2-Butyl-4-chloro-alpha-methyl-1-[[2'-[1-(triphenylmethyl)-1H-tetrazol-5-yl][1,1'-biphenyl-4-yl]methyl]-1H-imidazole-5-methanol To a solution of 0.679 g of the product of Example 2 in 10 ml of tetrahydrofuran, cooled to 0° C. is slowly added 0.705 ml of 3.0 M methylmagnesium bromide. The cooling bath is removed and reaction mixture allowed to warm to room temperature and stir for 2 hours. The reaction mixture is quenched with saturated ammonium chloride and diluted with water, followed by extraction with ethyl acetate. The organic layer is dried with MgSO$_4$, filtered and concentrated to give 0.06 g of the desired product as a solid. FAB MASS SPEC 701(M+Na).

EXAMPLE 4

1-[[2-Butyl-4-chloro-1-[[2'-[1-(triphenylmethyl)-1H-tetrazol-5yl][1,1'-biphenyl]-4-yl]methyl]-1H-imidazol-5-yl]-ethanone A suspension of 0.695 g of the product of Example 3 in 20 ml of 1,2-dichloroethane is sonicated under argon for 8 hours with 3.5 g of manganese dioxide, stirred at room temperature for 8 hours and filtered through diatomaceous earth which is washed with 250 ml of methylene chloride. The filtrate is concentrated in vacuo to give 0.454 g of the desired product as a solid. FAB MASS SPEC 699(M+Na).

EXAMPLE 5

2-Butyl-4-chloro-alpha,alpha-dimethyl-1-[[2'-[1-(triphenylmethyl)-1H-tetrazol-5-yl][1,1'-biphenyl]-4-yl]methyl]-1H-imidazole-5-methanol To a stirred solution of 0.444 g of the product of Example 4 in 10 ml of tetrahydrofuran, cooled to 0° C. is slowly added 0.656 ml of 3.0 M methylmagnesium bromide. The cooling bath is removed after 0.5 hour and reaction mixture allowed to warm to room temperature and stir for 2 hours. An additional 1.2 ml of 3.0 M methyl magnesium bromide is added and the reaction mixture stirred at room temperature for 0.5 hour. An additional 1.0 ml of 3.0 M methyl magnesium bromide is added an the reaction mixture stirred at room temperature for 0.5 hour. The reaction mixture is quenched with saturated ammonium chloride and diluted with water, followed by extraction with ethyl acetate. The organic layer is dried with MgSO$_4$, filtered and concentrated to give a crude solid which is purified by column chromatography on silica gel with 1:2 ethyl acetate-hexane to give 0.706 g of the desired product as a solid. FAB MASS SPEC 693(M+H).

EXAMPLE 6

5-[4'-[[2-Butyl-4-chloro-5-(1-methylethenyl)-1H-imidazol-1-yl]methyl][1,1'-biphenyl]-2-yl]-1-(triphenylmethyl-1H-tetrazole To a stirred solution of 0.256 g of the product of Example 5 in 2.0 ml of chloroform is added 0.497 g of {bis[α,α-bis(trifluoromethyl)benzenemethanolato]-diphenylsulfur} followed by stirring for 18 hours. The reaction mixture is diluted with chloroform and washed with 1 N NaOH, brine, dried over K$_2$CO$_3$ and concentrated in vacuo to a residue. The residue is purified by column chromatography using 1:3 ethyl acetate-hexane to give 0.160 g of the desired product as a solid. FAB MASS SPEC 675(M+H).

EXAMPLE 7

Cis-(+/−)-2-[2-Butyl-4-chloro-1-[[2'-[1-(triphenylmethyl)-1H-tetrazol-5-yl][1,1'-biphenyl]-4-yl]methyl]-1H-imidazol-5-yl]hexahydro-2-methyl-pyrrolo[1,5-b]isoxazole A mixture of 0.160 g of the product of Example 6 and an excess of 3,4-dihydro-2H-pyrrole 1-oxide in 15 ml of toluene is heated at reflux for 14 hours. The reaction mixture is concentrated in vacuo to a residue which is purified by column chromatography on silica gel using ethyl acetate to give 0.099 g of the desired product as a solid. FAB MASS SPEC 760(M+H).

EXAMPLE 8

Cis-(+/−)-2-[2-Butyl-4-chloro-1-[[2'-(1H-tetrazol-5-yl)[1,1'-biphenyl]-4-yl]methyl]-1H-imidazol-5-yl]hexahydro-2-methyl-pyrrolo[1,2-b]isoxazole A mixture of 0.079 g of the product of Example 7 in 1.0 ml of methanol and 5.0 ml of tetrahydrofuran is heated at reflux for 18 hours, cooled and concentrated in vacuo to a residue.which is purified by column chromatography on silica gel using chloroform/methanol (9:1) to give 0.045 g of the desired product as a solid. FAB MASS SPEC. 518(M+H).

Angiotensin II Antagonists In Vitro Tests

Materials and Methods

Beef adrenals are obtained from a local slaughter house (Maxwell-Cphen). [$^{125}$I](Sar$^1$,Ile$^8$)AngII, S.A. 2200 Ci/mmole, is purchased from Dupont (NEN ®, Boston, Mass.). All unlabeled AngII analogs, Dimethylsulfoxide (DMSO), nucleotides, bovine serum albumin (BSA) are purchased from Sigma Chemical Co., St. Louis, Mo. U.S.A.

Preparation of Membranes

Approximately sixteen (16) to twenty (20) beef adrenal glands are processed as follows: fresh adrenal glands received on crushed ice are cleaned of fatty tissues and the tough membranes encapsulating the glands are removed and discarded. The brownish tissue forming the adrenal cortex is scraped off and finely minced with scissors before homogenization. Care is taken to avoid contamination with medullary tissue during dissection. The scraped cortices are suspended in twenty volumes of an ice-cold buffer medium consisting of 10 mM Tris.HCl (pH 7.4 at 22° C.) and containing 1.0 mM EDTA and 0.2 M sucrose. Unless otherwise indicated, all subsequent operations are done at 4° C. The tissue is homogenized in a glass homogenizer with a motor-driven teflon pestle with a clearance of 1.0 mm. The homogenate is centrifuged first at low speed (3,000× g) for 10 min. The resulting pellet is discarded and the supernatant fluid recentrifuged at 10,000× g for 15 minutes to give a $P_2$ pellet. This $P_2$ pellet is discarded and the liquid phase is carefully decanted off in clean centrifuge tubes and recentrifuged at high speed (1000,000× g) for and the protein content of the preparation is determined by the Lowry's method (Lowry, O. H., Roseborough, N. F., Farr, A. L. and Randall, R. J., Protein measurement with Folin phenol reagent. J. Biol. Chem., 48, 265-275, 1951). The pelleted membrane is reconstituted in 50.0 mM Tris.HCl buffer containing 0.1 mM of phenylmethylsulfonyl fluoride (PMSF) to give approximately a protein concentration of 2.5 mg per ml of tissue suspension. The membrane preparation is finally aliquoted in 1.0 ml volumes and stored at −70° C. until use in the binding assays.

Receptor Binding Assay

Binding of [$^{125}$I](Sar$^1$, Ile$^8$)AngII

The binding of [125I](Sar$^1$,Ile$^8$)AngII to microsomal membranes is initiated by the addition of reconstituted membranes (1:10 vols.) in freshly made 50.0 mM Tris.HCl buffer, pH 7.4 containing 0.25% heat inactivated bovine serum albumin (BSA): 80 μl membrane protein (10 to 20 μg/assay) to wells already containing 100 μl of incubation buffer (as described above) and 20 μl [$^{125}$I](Sar$^1$,Ile$^8$)AngII (Specific Activity, 2200 Ci/m-mole). Non-specific binding is measured in the presence of 1.0 μM unlabeled (Sar$^1$,Ile$^8$)AngII, added in 20 μl volume. Specific binding for [$^{125}$I](Sar$^1$,Ile$^8$)AngII is greater than 90%. In competition studies, experimental compounds are diluted in dimethylsulfoxide (DMSO) and added in 20 μl to wells before the introduction of tissue membranes. This concentration of DMSO is found to have no negative effects on the binding of [$^{125}$I](Sar$^1$,Ile$^8$)AngII to the membranes. Assays are performed in triplicate. The wells are left undisturbed for 60 min. at room temperature. Following incubation, all wells are harvested at once with a Brandel ® Biomedical Research & Development Labs. Inc., Gaithersburg, Md., U.S.A.). The filter discs are washed with 10×1.0 ml of cold 0.9% NaCl to remove unbound ligand. Presoaking the filter sheet in 0.1% polyethyleneimine in normal saline (PEI/Saline) greatly reduces the radioactivity retained by the filter blanks. This method is routinely used. The filters are removed from the filter grid and counted in a Parkard ® Cobra Gamma Counter for 1 min. (Packard Instrument Co., Downers Grove, Ill., U.S.A.). The binding data are analyzed by the non-linear interactive "LUNDON-1" program (LUNDON SOFTWARE Inc., Cleveland, Ohio, U.S.A.). Compounds that displace 50% of the labelled angiotensin II at the screening dose of 50 μM are considered active compounds and are then evaluated in concentration-response experiments to determinded their $IC_{50}$ values. The results are shown in Table I.

TABLE I

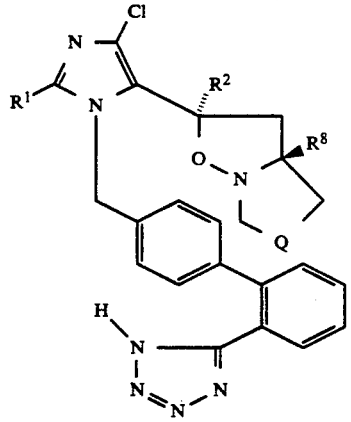

| Ex. No. | R$^1$ | R$^2$ | R$^8$ | Q | Antiotensin II Receptor Binding IC$_{50}$(M) |
|---|---|---|---|---|---|
| 8 | —(CH$_2$)$_3$CH$_3$ | —CH$_3$ | H | —CH$_2$— | 34 × 10$^{-9}$ |

The enzyme renin acts on a blood plasma alpha$_2$-globulin, angiotensinogen, to produce angiotensin I, which is then converted by angiotensin converting enzyme to AII. The substance AII is a powerful vasopressor agent which is implicated as causative agent for producing high blood pressure in mammals. Therefore, compounds which inhibit the action of the hormone angiotensin II (AII) are useful in alleviating angiotensin induced hypertension.

As can be seen from Table I, the compounds demonstrate excellent Angiotensin II Receptor Binding activity.

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds my be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin 1E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

What is claimed is:

1. An imidazole compound having the formula:

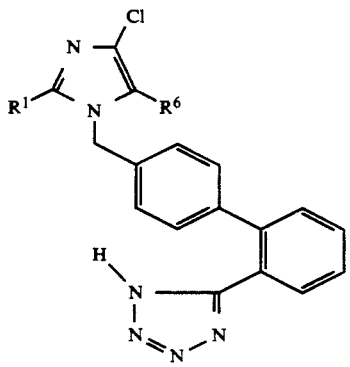

FORMULA I wherein:

$R^1$ is lower alkyl of 1 to 4 carbon atoms;
$R^6$ is

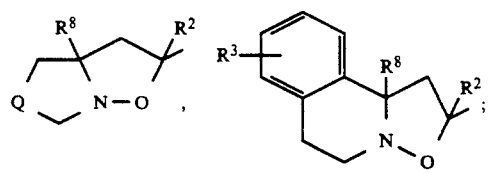

$R^2$ is hydrogen, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridinyl, thienyl, furanyl;

$R^8$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), —$CO_2R^7$;

$R^7$ is H, straight or branched chain lower alkyl of 1 to 4 carbon atoms;

Q is —$(CR^8R^8)_n$—;

n is 1 or 2;

$R^3$ is H, —$CH_3$, —$CF_3$, nitro, —$OCH_3$, F, Cl, Br; or the pharmaceutically acceptable salts thereof.

2. The compound according to claim 1 wherein said salts are selected from potassium, sodium, calcium, magnesium or ammonium.

3. The compound according to claim 1 wherein $R^1$ is a straight chain alkyl of 3 or 4 carbon atoms; and $R^2$ is —$CH_3$.

4. The compound according to claim 1 cis-(+/—)-2-[2-butyl-4-chloro-1-[[2'-(1H-tetrazol-5-yl)[1,1'-biphenyl]-4-yl]methyl]-1H-imidazol-5-yl]hexahydro-2-methyl-pyrrolo[1,2-b]isoxazole 5. A imidazole compound having the formula:

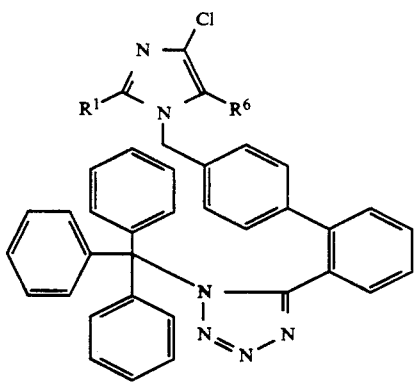

wherein:
$R^1$ is lower alkyl of 1 to 4 carbon atoms;
$R^6$ is

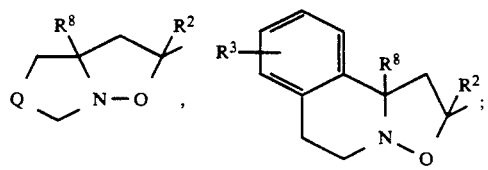

$R^2$ is hydrogen, lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), pyridinyl, thienyl, furanyl;

$R^8$ is H, straight chain lower alkyl of 1 to 4 carbon atoms, phenyl, substituted phenyl (substitution selected from mono-lower alkyl of 1 to 3 carbon atoms, trifluoromethyl, nitro, O-alkyl of 1 to 3 carbon atoms, F, Cl, or Br), —$CO_2R^7$;

$R^7$ is H, straight or branched chain lower alkyl of 1 to 4 carbon atoms;

Q is —$(CR^8R^8)_n$—;

n is 1 or 2;

$R^3$ is H, —$CH_3$, —$CF_3$, nitro, —$OCH_3$, F, Cl, Br.

6. A pharmaceutical composition useful for treating angiotensin induced hypertension or congestive heart failure in a mammal comprising a suitable pharmaceutical carrier and an effective amount of a compound of claim 1.

7. A method of treating angiotensin induced hypertension in a mammal comprising administering a compound of claim 1 to said mammal an amount effective to lower angiotensin induced hypertension.

8. A method of treating congestive heart failure in a mammal comprising administering a compound of claim 1 to said mammal in an amount effective to treat congestive heart failure.

9. A method of antagonizing the effects of Angiotensin II in a mammal comprising administering a compound of claim 1 to said mammal in an amount effective to treat the effects of Angiotensin II.

* * * * *